United States Patent
Yang

(10) Patent No.: US 10,774,144 B2
(45) Date of Patent: Sep. 15, 2020

(54) HUMAN PROGRAMMED CELL DEATH 1 RECEPTOR ANTIBODY, METHOD OF PREPARING SAME, AND USE THEREOF

(71) Applicant: HANGZHOU SUMGEN BIOTECHNOLOGY Co., Ltd., Zhejiang (CN)

(72) Inventor: Fan Yang, Beijing (CN)

(73) Assignee: Hangzhou Sumgen Biotechnology Co., Ltd, Zhejiang (CN)

( * ) Notice: Subject to any disclaimer, the term of this patent is extended or adjusted under 35 U.S.C. 154(b) by 113 days.

(21) Appl. No.: 16/066,024

(22) PCT Filed: Dec. 19, 2016

(86) PCT No.: PCT/CN2016/110790
§ 371 (c)(1),
(2) Date: Jun. 25, 2018

(87) PCT Pub. No.: WO2017/107885
PCT Pub. Date: Jun. 29, 2017

(65) Prior Publication Data
US 2019/0016799 A1 Jan. 17, 2019

(30) Foreign Application Priority Data
Dec. 23, 2015 (CN) .......................... 2015 1 0981105

(51) Int. Cl.
| C07K 16/28 | (2006.01) |
| A61P 37/04 | (2006.01) |
| A61P 35/00 | (2006.01) |
| C12N 15/62 | (2006.01) |
| A61K 39/00 | (2006.01) |

(52) U.S. Cl.
CPC .............. *C07K 16/28* (2013.01); *A61P 35/00* (2018.01); *A61P 37/04* (2018.01); *C07K 16/2818* (2013.01); *C12N 15/62* (2013.01); *A61K 2039/505* (2013.01); *C07K 2317/21* (2013.01); *C07K 2317/33* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS 8,008,449 B2 * 8/2011 Korman ................. A61K 51/10
530/388.15

FOREIGN PATENT DOCUMENTS

| CN | 101213297 B | 2/2013 |
| CN | 104987421 A | 10/2015 |
| CN | 105669864 A | 6/2016 |
| WO | 2004056875 A1 | 7/2004 |
| WO | 2015095404 A2 | 6/2015 |
| WO | 2015095418 A1 | 6/2015 |
| WO | 2015119930 A1 | 8/2015 |

OTHER PUBLICATIONS

Mariuzza, R.A. etal. The Structural Basis of Antigen-Antibody Recognition1 Annu. Rev. Biophys. Biphys. Chem. 16:139-159, 1987.*
MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response.1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Rao et al. 'Anti-PD-1/PD-L1 therapy for infectious diseases: learning from the cancer paradigm.' J. Infect. Dis. 56:221-228, 2017.*
Naidoo et al. 'Toxicities of the anti-PD-1 and anti-PD-L1 immune checkpoint antibodies.' Ann Onc. 26:2375-2391, 2015.*

* cited by examiner

*Primary Examiner* — Nora M Rooney
(74) *Attorney, Agent, or Firm* — Fox Rothschild LLP

(57) ABSTRACT

Disclosed are a human programmed cell death 1 receptor (hPD-1) antibody, a method of preparing the same, and use thereof. The preparation method comprises screening by using a natural antibody library screening platform to obtain a new human programmed cell death 1 receptor antibody. The antibody obtained by the screening step can specifically identify human PD-1 molecules and is used to inhibit mutual interactions between PD-1/PD-L1 and PD-1/PD-L2, thereby improving a level of an immune response.

14 Claims, 6 Drawing Sheets

Specification includes a Sequence Listing.

HUMAN PROGRAMMED CELL DEATH 1 RECEPTOR ANTIBODY, METHOD OF PREPARING SAME, AND USE THEREOF

TECHNICAL FIELD

The present invention relates to an antibody against human programmed death 1 receptor (hPD-1), a method of preparing the same, and use thereof.

BACKGROUND

Human programmed death 1 receptor (hPD-1) is an important class of immune negative regulatory molecules (also known as "immune checkpoint molecules"), which belongs to CD28 family, members of which also include CD28, CTLA4, ICOS and BTLA, and the like.

PD-1 is a type I transmembrane glycoprotein composed of three regions: an extracellular region, a transmembrane region and an intracellular region. Its extracellular membrane region is an immunoglobulin variable region (IgV)-like domain. The N-terminal of its intracellular region contains an immunoreceptor tyrosine based inhibitory motif (ITIM), and the C-terminal contains an immunoreceptor tyrosine based switch motif (ITSM), in which ITSM is the key motif for PD-1 molecules to transmit inhibitory signals into the cell. Unlike CTLA-4 and other family members, which present in the form of homodimers on the surface of T cells, PD-1 is expressed as a monomer on the surface of activated T cells, B cells, and myeloid cells and the like.

PD-1 has two ligands, i.e., PD-L1 (B7-H1, CD274) and PD-L2 (B7-DC, CD273), which belong to transmembrane molecules of B7 family. PD-L1 widely distributes on the surface of hematopoietic cells such as mature macrophages, B cells, dendritic cells, as well as non-hematopoietic cells such as endothelial cells, islet cells, and mast cells, and is highly expressed on the surface of various tumor cells; PD-L2 is only expressed on the surface of some cells such as macrophages, dendritic cells, and some B cell subtypes. Similar to cytotoxic T-lymphocyte-associated antigen 4 (CTLA-4), a classical immune negative regulatory molecule, PD-1 exerts immune negative regulation through its interaction with its ligands PDL1 and PDL2. When PD-1 interacts with its ligands, its intracellular segment ITSM is phosphorylated and recruits corresponding phosphorylating enzymes SHP-1 and SHP-2, resulting in dephosphorylation of downstream signaling molecules, thereby downregulating the immune cell response level. This negative regulatory mechanism of the immune system is a key molecular basis for maintaining immune tolerance of the body. However, a number of studies have shown that the overexpression of the immune negative regulatory molecules such as PD-1 and the immunosuppressive state of the body induced by its interaction with receptor PD-L1/PD-L2 plays an important role in the pathogenetic processes of cancers and chronic infectious diseases such as HIV, HCV, and HBV, and the like. By blocking the interaction between PD-1/PD-L1, the immunosuppression can be reversed, and the ability of the immune system to kill viruses and tumor cells may be enhanced; the effect of reversing the immunosuppressive state is better if PD-1/PD-L2 interaction is blocked simultaneously. Therefore, the targeting to such negative regulatory molecules has become a new cancer treatment strategy, and studies on PD1/PDL1 pathway inhibitors have attracted much attention. Antibody drugs that specifically block the PD1/PDL1 signaling pathway are the focus of the research in this area. PD1 antibodies Nivolumab (Opdivo, Bristol-Myers Squibb) and Pembrolizumab (Keytruda, Merck) both received FDA breakthrough therapy designations and were approved for marketing. Among them, Nivolumab of Bristol-Myers Squibb was approved by the FDA for marketing in December 2014, for clinical treatment of melanoma; then in March 2015, this antibody was approved by FDA for the treatment of squamous non-small cell lung cancer, indicating that such immunotherapies officially entered the field of clinical treatment of solid tumors.

There remains a need in the field for antibody drugs that specifically block the PD1/PDL1 signaling pathway.

SUMMARY OF THE INVENTION

A first aspect of the present invention relates to an isolated anti-human programmed death 1 receptor (anti-hPD-1) antibody or an antigen-binding fragment thereof, wherein a CDR1 sequence of a heavy chain variable region thereof is set forth in SEQ ID NO: 1, a CDR2 sequence is set forth in SEQ ID NO: 2, a CDR3 sequence is set forth in SEQ ID NO: 3; and/or a CDR1 sequence of a light chain variable region thereof is set forth in SEQ ID NO: 4, a CDR2 sequence is set forth in SEQ ID NO: 5, a CDR3 sequence is set forth in SEQ ID NO: 6; or the CDR sequences of the heavy or light chain are variant sequences having at least 70% homology, such as at least 75%, 80%, 85%, 90%, 91%, 92% homology, to the sequences set forth in SEQ ID NOs: 1-6 respectively and retaining biological activities of corresponding parent sequences; or the CDR sequences of the heavy or light chain are variant sequences obtainable by deletion, substitution, and/or addition of one or more amino acid residue(s), such as 1, 2, 3, 4 or 5 amino acid residue(s), of the sequences set forth in SEQ ID NOs: 1-6 respectively and retaining the biological activities of corresponding parent sequences.

In some embodiments, the anti-hPD-1 antibody or the antigen-binding fragment thereof comprises the heavy chain CDR1, CDR2, and CDR3 and the light chain CDR1, CDR2, and CDR3 as described above.

In some embodiments, a heavy chain variable region sequence of the anti-hPD-1 antibody or the antigen-binding fragment thereof is set forth in SEQ ID NO: 7; and/or a light chain variable region sequence thereof is set forth in SEQ ID NO: 8; or the heavy or light chain variable region sequences are variant sequences having at least 70% homology, such as at least 75%, 80%, 85%, 90%, 95%, 96%, 97%, 98%, 99%, or 99.1% homology, to the sequences set forth in SEQ ID NOs: 7-8 respectively and retaining the biological activities of corresponding parent sequences; or the heavy or light chain variable region sequences are variant sequences obtainable by deletion, substitution, and/or addition of one or more amino acid residue(s), such as 1, 2, 3, 4, 5, 10, 15, 20, 30, or 50 amino acid residue(s), of the sequences set forth in SEQ ID NOs: 7-8 respectively and retaining the biological activities of corresponding parent sequences.

In some embodiments, a heavy chain amino acid sequence of the anti-hPD-1 antibody or the antigen-binding fragment thereof is set forth in SEQ ID NO: 13 or 16; and/or a light chain variable region sequence thereof is set forth in SEQ ID NO: 11; or the heavy or light chain amino acid sequences are variant sequences having at least 70% homology, such as at least 75%, 80%, 85%, 90%, 95%, 96%, 97%, 98%, 99%, 99.1%, 99.2%, 99.3%, 99.4%, 99.5%, 99.6%, 99.7% or 99.8% homology, to the sequences set forth in SEQ ID NOs: 13, 16 or 11 respectively and retaining the biological activities of corresponding parent sequences; or the heavy or light chain amino acid sequences are variant sequences obtainable by deletion, substitution, and/or addition of one or more amino acid residue(s), such as 1, 2, 3, 4, 5, 10, 15, 20, 30, 50, or 100 amino acid residue(s), of the sequences set forth in SEQ ID NOs: 13, 16 or 11 respectively and retaining the biological activities of corresponding parent sequences.

In some embodiments, the anti-hPD-1 antibody or the antigen-binding fragment thereof is a full-length antibody, and preferably, a full-length antibody of an IgG1 or IgG4 isotype.

In some embodiments, the anti-hPD-1 antibody or the antigen-binding fragment thereof is an antigen-binding fragment, and preferably, a Fab fragment, a Fab'2 fragment or a single-chain antibody.

A second aspect of the present invention relates to a composition comprising the anti-hPD-1 antibody or the antigen-binding fragment thereof according to the first aspect as described above.

A third aspect of the present invention relates to a nucleic acid molecule encoding the anti-hPD-1 antibody or the antigen-binding fragment thereof according to the first aspect as described above.

In some embodiments, the nucleic acid molecule has a sequence set forth in SEQ ID NO: 9 or 10, or is a variant molecule having at least 70% homology, such as at least 75%, 80%, 85%, 90%, 95%, 96%, 97%, 98%, 99%, 99.1%, 99.2%, 99.4%, 99.5%, 99.6%, or 99.7% homology, to SEQ ID NO: 9 or 10 and still having the activity to encode the present antibody or the antigen-binding fragment thereof; or is a nucleic acid molecule that is completely complementary to or hybridizes to, under moderately to highly stringent conditions, a nucleic acid molecule having a sequence set forth in SEQ ID NO: 9 or 10. One example of the moderately stringent conditions includes the following: pre-washing in a solution of 5×SSC, 0.5% SDS, 1.0 mM EDTA (pH 8.0); hybridization at 50-60° C., 5×SSC, overnight; and then washing twice with 2×, 0.5×, and 0.2×SSC containing 0.1% SDS, respectively, for 20 min at 65° C. Suitable highly stringent hybridization conditions include the above conditions except that the hybridization temperature is increased, for example, to 60-65° C. or 65-70° C.

In some embodiments, the nucleic acid molecule has a sequence set forth in SEQ ID NO: 12 or 14; or is a variant molecule having at least 70% homology, such as at least 75%, 80%, 85%, 90%, 95%, 96%, 97%, 98%, 99%, 99.1%, 99.2%, 99.4%, 99.5%, 99.6%, 99.7%, 99.8%, 99.9% homology or higher, to SEQ ID NO: 12 or 14, and still having the activity to encode the present antibody or the antigen-binding fragment thereof; or is a nucleic acid molecule completely complementary to or hybridizes to, under moderately to highly stringent conditions, a nucleic acid molecule having a sequence set forth in SEQ ID NO: 12 or 14. One example of the moderately stringent conditions includes the following: pre-washing in a solution of 5×SSC, 0.5% SDS, 1.0 mM EDTA (pH 8.0); hybridization at 50-60° C., 5×SSC, overnight; and then washing twice with 2×, 0.5×, and 0.2×SSC containing 0.1% SDS, respectively, for 20 min at 65° C. Suitable highly stringent hybridization conditions include the above conditions except that the hybridization temperature is increased, for example, to 60-65° C. or 65-70° C.

A fourth aspect of the present invention relates to an expression vector comprising the nucleic acid molecule according to the third aspect as described above. The expression vector of the present invention is not particularly limited as long as it can express the antibody or the antigen-binding fragment thereof as claimed in the present invention.

A fifth aspect of the present invention relates to a host cell comprising the expression vector according to the fourth aspect as described above.

A sixth aspect of the present invention relates to a method of preparing the antibody or the antigen-binding fragment thereof according to the first aspect, comprising the steps of: expressing the host cell according to the fifth aspect under a culture condition suitable for expression of the anti-hPD-1 antibody or the antigen-binding fragment thereof, optionally, purifying the expressed antibody or the antigen-binding fragment thereof.

A seventh aspect of the present invention relates to use of the antibody or the antigen-binding fragment thereof according to the above first aspect in the manufacture of an agent for regulating immune response in a mammal, including human.

In other words, the present invention obtains a novel anti-hPD-1 antibody SG001 by utilizing a natural antibody library screening platform, which is able to specifically recognize human and monkey PD-1 molecules, to block PD-1/PD-L1 and PD-1/PD-L2 interactions, to regulate the immune response, and to increase the immune response level. The anti-human PD-1 antibody of the present invention specifically binds to human PD1 and shows superior properties. These properties include high binding affinity to human PD-1, but no cross-reactivity with other CD28 family members such as CD28, CTLA4, BTLA, and ICOS, and the like.

In some embodiments, the invention relates to an anti-human PD-1 antibody or an antigen-binding portion thereof, which exhibits at least one of the properties of:

(1) binding to human PD-1 with a $K_D$ of $1\times10^{-7}$M or less;

(2) insignificantly binding to CD28, CTLA4, BTLA, and ICOS, and the like;

(3) increasing the expression level of interferon γ in an MLR experiment;

(4) binding to monkey PD-1 with a $K_D$ of $1\times10^{-7}$M or less;

(5) inhibiting the binding of PD-L1 and/or PD-L2 to PD-1;

(6) stimulating the immune response.

The anti-human PD-1 antibody or the antigen-binding portion thereof of the present invention is particularly advantageous in that their activities of blocking PD1/PDL1 are significantly improved compared to those in the prior art. For example, their activities of blocking PD1/PDL1 are increased by 6 folds compared to BMS01 of the prior art (as shown in Example 6 and FIG. 6, the half inhibitory dosage for SG001 antibody was 1.471-0.227 μg/mL, which was significantly superior to that for positive antibody BMS01 (10.62±0.536 μg/mL), P<0.0001). The anti-human PD-1 antibody or the antigen-binding portion thereof of the present invention is also advantageous in that their expression levels in an eukaryotic expression system are significantly increased as compared to those of the anti-human PD-1 antibody or the antigen-binding portion thereof in the prior art. In some embodiments, the expression level is increased by at least 50%, or at least 100%. In some embodiments, the expression level is increased by at least 150%, at least 200%, at least 300%, or at least 400%. In some embodiments, the eukaryotic expression system is a mammalian cell expression system. In some embodiments, the mammalian cell is selected from the group consisting of Chinese hamster ovary (CHO) cells, baby hamster kidney (BHK) cells, COS cells, mouse NS0 thymoma cells, and mouse myeloma SP2/0 cells, and the like. In some embodiments, the mammalian cell is a CHO cell. The eukaryotic expression vectors in the art all may be used for the expression of the anti-human PD-1 antibody or the antigen binding portion thereof of the present invention. In some embodiments, the eukaryotic expression vector is selected from the group consisting of a pCMVp-NEO-BAN vector, a pEGFP enhanced green fluorescent protein expression vector, a pEGFT-Actin enhanced green fluorescent protein/human actin expression vector, a pSV2 expression vector, a CMV4 expression vector, pCMV-163, and the like. In some embodiments, the eukaryotic expression vector is pCMV-163.

Certain embodiments of the present invention relate to an anti-hPD-1 antibody or an antigen-binding portion thereof, wherein a CDR1 sequence of a heavy chain variable region thereof is set forth in SEQ ID NO: 1, a CDR2 sequence is set forth in SEQ ID NO: 2, a CDR3 sequence is set forth in SEQ ID NO: 3; and/or a CDR1 sequence of a light chain variable region thereof is set forth in SEQ ID NO: 4, a CDR2 sequence is set forth in SEQ ID NO: 5, a CDR3 sequence is set forth in SEQ ID NO: 6; or the heavy or light chain variable region CDRs are variant sequences having at least 70% homology, such as at least 80%, 85%, 90%, 95%, 96%, 97%, 98%, 99% sequence homology, to the sequences set forth in SEQ ID NOs: 1-6 and retaining the biological activities of corresponding parent sequences; or the heavy or light chain variable region CDRs are variant sequences obtainable by deletion, substitution, and/or addition of one or more amino acid residue(s), such as 1, 2, 3, 4, 5, 6, 7, 8, 9 or 10 amino acid residue(s), of the sequences set forth in SEQ ID NOs: 1-6, and retaining the biological activities of corresponding parent sequences.

In certain embodiments, the anti-human PD-1 antibody or the antigen-binding fragment thereof of present invention comprises the heavy chain CDR1, CDR2, and CDR3 and the light chain CDR1, CDR2, and CDR3 as described above.

In certain embodiments, the heavy chain variable region sequence of the present antibody is set forth in SEQ ID NO: 7; and/or the light chain variable region sequence is set forth in SEQ ID NO: 8; or the heavy or light chain variable region sequences are variant sequences having at least 70% homology, such as at least 80%, 85%, 90%, 95%, 96%, 97%, 98%, 99% sequence homology, to the sequences set forth in SEQ ID NOs: 7-8 and retaining the biological activities of corresponding parent sequences; or the heavy or light chain variable region sequences are variant sequences obtainable by deletion, substitution, and/or addition of one or more amino acid residue(s), such as 1, 2, 3, 4, 5, 6, 7, 8, 9 or 10 amino acid residue(s), of the sequences set forth in SEQ ID NOs: 7-8, and retaining the biological activities of corresponding parent sequences.

In certain embodiments, the antibody of the present invention is a full-length antibody, such as but not limited to a full-length antibody of an IgG1 or IgG4 isotype; or an antigen-binding fragment, such as but not limited to a Fab fragment, a Fab'2 fragment, a single-chain antibody and the like.

Another aspect of the present invention relates to a composition comprising a therapeutically effective amount of the anti-hPD-1 antibody or the antigen-binding fragment thereof of the present invention. The composition comprises for example, but not limited to, an immunoconjugate, a bispecific molecule, and a pharmaceutically acceptable carrier, and the like. The composition of the present invention may also comprise another active ingredient, such as another active ingredient for regulating immune response in a subject.

A further aspect of the present invention relates to a nucleic acid molecule encoding the anti-hPD-1 antibody or the antigen-binding portion thereof of the present invention. In certain embodiments, the nucleic acid molecule has a sequence set forth in SEQ ID NO: 9 or 10; or is a variant molecule having at least 70% homology to SEQ ID NO: 9 or 10, and still having the capability of encoding the present antibody or the antigen-binding fragment thereof; or is a nucleic acid molecule completely complementary to or hybridizes to, under moderately to highly stringent conditions, a nucleic acid molecule having a sequence set forth in SEQ ID NO: 9 or 10. In some embodiments, the stringent hybridization conditions are for illustrative purposes, and suitable moderately stringent conditions for testing hybridization of the polynucleotides of the present invention to other polynucleotides include the following: pre-washing in a solution of 5×SSC, 0.5% SDS, 1.0 mM EDTA (pH 8.0); hybridization at 50-60° C., 5×SSC, overnight; and then washing twice with 2×, 0.5×, and 0.2×SSC containing 0.1% SDS, respectively, for 20 min at 65° C. Suitable highly stringent hybridization conditions include the above conditions except that the hybridization temperature is increased, for example, to 60-65° C. or 65-70° C.

Another aspect of the invention relates to an expression vector comprising such a nucleic acid molecule. In certain embodiments, the expression vector is a prokaryotic expression vector or a eukaryotic expression vector. In certain embodiments, the expression vector is a eukaryotic expression vector. In certain embodiments, the eukaryotic expression vector is selected from the group consisting of a pCMVp-NEO-BAN vector, a pEGFP enhanced green fluorescent protein expression vector, a pEGFT-Actin enhanced green fluorescent protein/human actin expression vector, a pSV2 expression vector, a CMV4 expression vector, pCMV-163, and the like. In some embodiments, the eukaryotic expression vector is pCMV-163.

A further aspect of the invention relates to a host cell comprising such an expression vector. In certain embodiments, the host cell is selected from the group consisting of bacteria, fungi, actinomycete, insect cells, and mammalian cells. In certain embodiments, the host cell is a mammalian cell. More specifically, the mammalian cell is selected from the group consisting of Chinese hamster ovary (CHO) cells, small hamster kidney (BHK) cells, COS cells, mouse NSO thymoma cells and mouse myeloma SP2/0 cells, and the like.

One aspect of the present invention relates to a method for producing the antibody or the antigen-binding fragment thereof of the present invention, comprising the steps of: expressing the above-described host cell comprising the expression vector of the present invention under a culture condition suitable for expression of the anti-hPD-1 antibody or the antigen-binding fragment thereof, optionally, purifying the expressed antibody or the antigen-binding fragment thereof. Suitable culture conditions for the expression of an antibody or an antigen-binding fragment thereof are known to those skilled in the art.

Another aspect of the present invention relates to a method of regulating immune response in a mammal including human by using the anti-human PD-1 antibody or the antigen-binding fragment thereof, comprising the steps of administering the antibody or the antigen-binding fragment thereof of the present invention to a mammal including human, such that the immune response of the mammal including human is regulated. The regulation includes enhancement, increase, or stimulation of the immune response.

One aspect of the present invention relates to use of the anti-human PD-1 antibody or the antigen-binding fragment thereof in the manufacture of an agent for regulating immune response in a mammal, including human.

One aspect of the present invention relates to the anti-human PD-1 antibody or the antigen-binding fragment thereof for use to regulate the immune response in a mammal, including human.

The anti-hPD-1 antibody or the antigen-binding fragment thereof of the present invention is able to specifically recognize human and monkey PD-1 molecules, to block PD-1/PD-L1 and PD-1/PD-L2 interactions, to regulate the immune response, and to increase the immune response level. The anti-human PD-1 antibody of the present invention specifically binds to human PD1 and shows superior properties. These properties include high binding affinity to human PD-1, but no cross-reactivity with other CD28 family members such as CD28, CTLA4, BTLA, and ICOS, and the like. The anti-human PD-1 antibody or the antigen-binding portion thereof of the present invention is particularly advantageous in that their activities of blocking PD1/PDL1 are significantly improved as compared to those in the prior art. The anti-human PD-1 antibody or the antigen-binding portion thereof of the present invention is also advantageous in that their expression levels in an eukaryotic expression system are significantly increased as compared to those of the anti-human PD-1 antibody or the antigen-binding portion thereof in the prior art.

DETAILED DESCRIPTION

Definition

Figure 1:
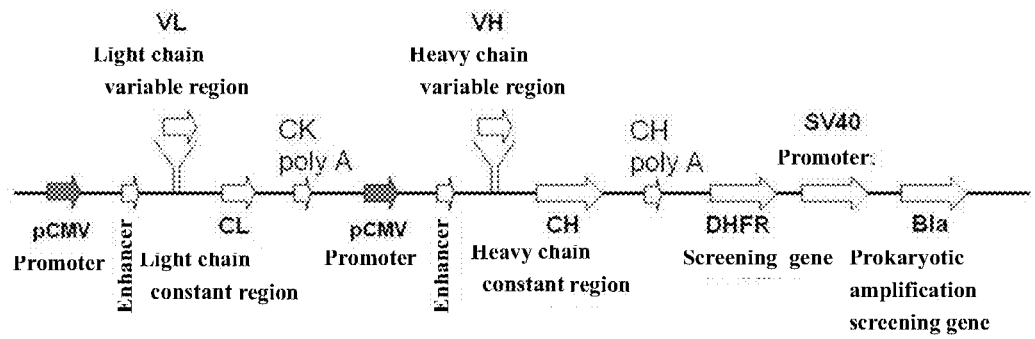
FIG. 1 shows the physical map of the expression vector pCMV-163.

The term "antibody" as used herein includes monoclonal antibodies, polyclonal antibodies, multispecific antibodies (e.g., bispecific antibodies and multireactive antibodies), and antibody fragments. Thus, the term "antibody" as used in any context within this specification includes, but is not limited to, any specific binding member, immunoglobulin class, and/or isotype (e.g., IgG1, IgG2, IgG3, IgG4, IgM, IgA, IgD, IgE, and IgM); and biologically relevant fragments or specific binding members thereof, including but not limited to Fab, F(ab')2, Fv, and scFv (single-chain or related entity). It is understood in the art that antibodies are glycoproteins comprising at least two heavy (H) chains and two light (L) chains inter-connected by disulfide bonds, or antigen-binding portions thereof. A heavy chain consists of a heavy chain variable region (VH) and a heavy chain constant region (CH1, CH2, and CH3). A light chain consists of a light chain variable region (VL) and a light chain constant region (CL). The variable regions of both the heavy and light chains comprise framework regions (FWR) and complementarity determining regions (CDRs). The four FWR regions are relatively conserved, while the CDR regions (CDR1, CDR2, and CDR3) represent hypervariable regions, and are arranged from the NH2 terminus to the COOH terminus as follows: FWR1, CDR1, FWR2, CDR2, FWR3, CDR3, FWR4. The variable regions of the heavy and light chains contain a binding domain that interacts with an antigen while, depending on the isotype, the constant region(s) may mediate the binding of the immunoglobulin to host tissues or factors.

Meanwhile, the "antibody" as defined herein also includes chimeric antibodies, humanized antibodies, and recombinant antibodies, human antibodies generated from transgenic non-human animals, as well as antibodies selected from libraries using enrichment techniques available to those skilled in the art.

The term "variable" refers to extensive differences in the sequences of certain segments of the variable (V) regions among antibodies. The V domain mediates antigen binding and defines specificity of a particular antibody for its particular antigen. However, the variability is not evenly distributed across the 110-amino acids span of the variable region. Instead, the V regions consist of stretches called framework regions (FRs) which are relative invariant and have 15-30 amino acids, separated by shorter regions of extreme variability called "hypervariable regions" each having a length of 9-12 amino acids. The variable regions of native heavy and light chains each comprises four FRs, largely adopting a β-sheet configuration, connected by three hypervariable regions, which form loops connecting, and in some cases forming part of, the β-sheet structure. The hypervariable regions in each chain are held together in a close proximity by the FRs and, contribute to the formation of the antigen-binding site of antibodies together with the hypervariable regions from other chains.

The term "hypervariable region" as used herein refers to the amino acid residues of an antibody that are responsible for antigen binding. The hypervariable region generally contains amino acid residues from a "complementarity determining region" ("CDR").

The term "monoclonal antibody" as used herein refers to an antibody obtained from a population of substantially homogeneous antibodies, i.e., the individual antibodies comprising population are identical except for possible naturally occurring mutations that may be present in a minor amount. The term "polyclonal antibody" refers to a preparation that includes different antibodies directed against different determinants ("epitopes").

The monoclonal antibodies herein include "chimeric" antibodies, in which a portion of the heavy chain and/or light chain is identical with or homologous to the corresponding sequences in an antibody derived from a particular species or belonging to a particular antibody class or subclass, while the remainder of the chain(s) is identical with or homologous to the corresponding sequences in an antibody derived from another species or belonging to another antibody class or subclass, and a fragment of such an antibody, so long as they exhibit the desired biological activities. The present invention provides a variable region antigen-binding sequence derived from a human antibody. Thus, chimeric antibodies of primary interest herein include an antibody having one or more human antigen-binding sequences (such as CDRs) and containing one or more sequences derived from a non-human antibody such as an FR or C region sequence. In addition, the chimeric antibody described herein is an antibody comprising a human variable region antigen binding sequence of one antibody class or subclass and another sequence from another antibody class or subclass such as an FR or a C region sequence.

A "humanized antibody" is generally a human antibody having one or more amino acid residues introduced into it from a non-human source. These non-human amino acid residues are often referred to as "import" residues, which are typically taken from an "import" variable region.

An "antibody fragment" comprises a portion of an intact antibody, such as the antigen binding portion or a fragment or a variable region of the intact antibody. The antigen binding portion or fragment or variable region of the intact antibody includes, but are not limited to, Fab, Fab', F(ab')2, and Fv fragments; diabodies; linear antibodies; single-chain antibody molecules; and multispecific antibodies formed from antibody fragments.

"Fv" is the minimum antibody fragment that contains a complete antigen-recognition and antigen-binding site. This fragment comprises a dimer of one heavy- and one light-chain variable region domain in tight, non-covalent association. Six hypervariable loops (three loops each formed from the H and L chains) are generated from the folding of these two domains, which provide the amino acid residues for antigen binding and confer the antibody with antigen-binding specificity. However, even a single variable region (or half of an Fv, which contains only 3 antigen-specific CDRs) has the ability to recognize and bind an antigen, although at a lower affinity than the entire binding site.

"single-chain Fv" ("sFv" or "scFv") is an antibody fragment comprising the VH and VL antibody domains connected into a single polypeptide chain. The sFv polypeptide can further comprise a polypeptide linker between the VH and the VL domains that enables the sFv to form the desired structure for antigen binding.

The term "diabody" refers to a small antibody fragment prepared by constructing sFv fragments between VH and VL domains with short linkers (about 5-10 residues), such that inter-chain rather than intra-chain pairing of the V domains is achieved to form a bivalent fragment, i.e., a fragment having two antigen-binding sites. A bispecific diabody is a heterodimer of two "crossover" sFv fragments, in which the VH and VL domains of the two antibodies are present on different polypeptide chains.

Domain antibodies (dAbs), which can be produced in fully human form, are the smallest known antigen-binding fragments of antibodies, ranging from about 11 kDa to about 15 kDa. dAbs are the variable regions of the heavy and light chains (VH and VL, respectively) of immunoglobulins. They are highly expressed in microbial cell cultures and show favorable biophysical properties including, for example but not limited to, solubility and temperature stability, and are well suited for screening and affinity maturation by in vitro selection systems, such as phage display. dAbs are bioactive as monomers and, owing to their small size and inherent stability, can be formatted into larger molecules to create drugs with prolonged serum half-lives or other pharmacological activities.

Fv and the sFv are the only species with intact binding sites that are devoid of constant regions. Therefore, they are suitable for reduced non-specific binding during in vivo use. An sFv fusion protein can be constructed to yield fusion of an effector protein at either the amino terminus or the carboxy terminus of an sFv. The antibody fragments can also be "linear antibodies". Such linear antibody fragments can be monospecific or bispecific.

Other modifications of the antibody are also contemplated herein. For example, the antibody can be linked to one of a variety of nonproteinaceous polymers, such as polyethylene glycol, polypropylene glycol, polyoxyalkylenes, or copolymers of polyethylene glycol and polypropylene glycol. The antibody can also be entrapped in a microcapsule prepared, for example, by coacervation techniques or by interfacial polymerization, in colloidal drug delivery systems (e.g., liposomes, albumin microspheres, microemulsions, nanoparticles and nanocapsules), or in macroemulsions.

Typically, the antibodies of the present invention are produced recombinantly, using vectors and methods available in the art. Human antibodies can also be generated by in vitro activated B cells. Human antibodies can also be produced in a transgenic animal (such as a mouse), which is capable of producing a full repertoire of in the absence of endogenous immunoglobulin production.

Antibody fragments were derived via proteolytic digestion of intact antibodies. However, these fragments can also be produced directly by recombinant host cells. Fab, Fv, and ScFv antibody fragments can all be expressed in and secreted from E. coli, thus, large amounts of such fragments can be easily generated. Fab'-SH fragments can be directly recovered from E. coli and chemically coupled to form F(ab')2 fragments. The techniques for producing antibody fragments will be apparent to the skilled practitioner.

Variant antibodies are also included within the scope of the present invention. Therefore, variants of the sequences recited in the application are also included within the scope of the present invention. Further variants of the antibody sequences with improved affinity can be obtained by using methods known in the art and are also included within the scope of the invention. For example, amino acid substitutions can be used to obtain antibodies with further improved affinity. Alternatively, codon optimization of the nucleotide sequence can be used to improve the translation efficiency in expression systems for antibody production.

Such variant antibody sequences will share a sequence identity of 70% or more (e.g., 80%, 85%, 90%, 95%, 97%, 98%, 99% or greater) with the sequences recited in the application. Such sequence identity is calculated with regard to the full length of the reference sequences (i.e., the sequences recited in the application).

The term "polypeptide" is used in its conventional meaning, i.e., as a sequence of amino acids. The polypeptide is not limited to a product of a specific length. Peptides, oligopeptides, and proteins are all included within the definition of a polypeptide, and such terms can be used interchangeably herein unless specifically indicated otherwise. This term also includes post-expression modifications of the polypeptide, such as glycosylation, acetylation, phosphorylation, and the like, as well as other modifications known in the art, both naturally occurring and non-naturally occurring. A polypeptide can be an entire protein, or a subsequence thereof. Particular polypeptides of interest in the context of the present invention are amino acid subsequences containing CDRs, VHs and VLs, being capable of binding hPD-1.

The term "variant" of a polypeptide as used herein is a polypeptide having one or more substitutions, deletions, additions, and/or insertions, which is typically different from the polypeptides specifically disclosed herein. Such variants can be naturally occurring or synthetically generated, for example, by modifying one or more of the above polypeptide sequences of the invention, and assessing one or more biological activities of the polypeptides as described herein and/or using any of a number of well-known techniques in the art.

For example, certain amino acids can be substituted for other amino acids in a protein structure without appreciable loss of its ability to bind other polypeptides (such as antigens) or cells. Since it is the binding capability and nature of a protein that define that protein's biological functional activity, certain amino acid sequence substitutions can be made in a protein sequence, thereby obtaining a protein with similar properties. Thus, it is contemplated that various changes can be made in the peptide sequences of the disclosed composition or corresponding DNA sequences encoding the peptides without significant loss of their biological utility or activity.

In many cases, a polypeptide variant will contain one or more conservative substitutions. A "conservative substitution" refers to one in which an amino acid is substituted for another amino acid having similar properties, such that one skilled in the art of peptide chemistry would expect that the secondary structure and hydrophilic property of the polypeptide will substantially unchange.

Amino acid substitutions are generally based on the relative similarity of the amino acid side-chain substituents, such as their hydrophobicity, hydrophilicity, charge, size, and the like. Exemplary substitutions considering the various foregoing characteristics are well known to those skilled in the art and include: arginine and lysine; glutamate and aspartate; serine and threonine; glutamine and asparagine; and valine, leucine and isoleucine.

"Homology" or "sequence identity" refers to the percentage of residues in a polynucleotide or polypeptide sequence variant and a non-variant sequence after sequence alignment and introduction of gaps. In a particular embodiment, polynucleotide and polypeptide variants have at least about 70%, at least about 75%, at least about 80%, at least about 90%, at least about 95%, at least about 98%, or at least about 99% polynucleotide or polypeptide homology with the polynucleotides or polypeptides described herein.

Such variant polypeptide sequences will share a sequence identity of 70% or more (i.e., 80%, 85%, 90%, 95%, 97%, 98%, 99% or more) with the sequences recited in the application. In additional embodiments, the present invention provides polypeptide fragments comprising contiguous stretches of various lengths of amino acid sequences disclosed herein. For example, where applicable, peptide sequences provided herein comprise at least about 5, 10, 15, 20, 30, 40, 50, 75, 100, 150, or more contiguous peptides of one or more of the sequences disclosed herein as well as all intermediate lengths therebetween.

Vectors of the present invention include those capable of replication in any type of cells or organisms, including, for example, plasmids, phages, cosmids, and mini-chromosomes. In some embodiments, vectors comprising a polynucleotides of the present invention are vectors suitable for propagation or replication of the polynucleotides, or vectors suitable for expression of a polypeptides of the present invention. Such vectors are known in the art and commercially available.

"Vector" includes shuttle and expression vectors. Typically, the plasmid constructs also will include an origin of replication (such as the ColE1 origin of replication) and a selectable marker (such as ampicillin or tetracycline resistance), for replication selection respectively, of the plasmid in bacteria. An "expression vector" refers to a vector comprising the control sequences or regulatory elements required for expression of the antibodies including antibody fragments of the invention, in bacterial or eukaryotic cells.

The term "cell" as used herein can be any cell, including but not limited to eukaryotic, multicellular species (as opposed to unicellular yeast cells), for example, but not limited to, mammalian cells or human cells. The cells can be present as a single entity, or as part of a larger cell population. Such "larger cell populations" can include, for example, cell cultures (either mixed or pure), tissues (such as endothelial, epithelial, mucosal, or other tissues), organs (such as lung, liver, muscle, and other organs), organ systems (such as circulatory system, respiratory system, gastrointestinal system, urinary system, nervous system, integumentary system, or other organ systems) or organisms (such as birds, mammals, or the like).

The term "high affinity binding" of the present invention refers to that the anti-hPD-1 antibody binds to the human PD-1 with a $K_D$ of $1\times10^{-7}$ M or less, for example, a $K_D$ of at least $1\times10^{-7}$ M, $1\times10^{-8}$ M, $1\times10^{-9}$ M, $1\times10^{-10}$ M, and $1\times10^{-11}$M.

The term "insignificantly binding to CD28, CTLA4, BTLA, ICOS, and the like" of the present invention refers to that the proportion of the anti-hPD-1 antibody binding to the human PD-1 is at least 10 times, for example, at least 10, 15, 20, 25, 30, 35, 40, 45, 50, 60, 70, 80, 90, 100, 150, 200, 300, 500, 1000, 5000, 10000 times or more higher than that of the binding to CD28, CTLA4, BTLA, and ICOS, and the like.

Where a value of ranges is provided, it is understood that each intervening value, to the tenth of the unit of the lower limit unless the context clearly dictates otherwise, between the upper and lower limit of that range and any other stated or intervening value in that stated range, is encompassed within the scope of the present invention. The upper and lower limits of these smaller ranges which may independently be included in the smaller ranges are also encompassed within the present invention, subject to any specifically excluded limit in the stated range. Where the stated range includes one or both of the limits, ranges excluding either or both of those included limits are also included in the present invention.

Unless defined otherwise, all technical and scientific terms used herein have the same meanings as commonly understood by one of ordinary skill in the art to which this invention belongs. Although any methods and materials similar or equivalent to those described herein can also be used in the practice or testing of the present invention, the preferred methods and materials are now disclosed. All publications mentioned herein are incorporated herein by reference in their entirety.

On one hand, examples are provided in the present invention for describing the preparation process of the antibody of the present invention, and the preparation process is merely illustrative of related methods, but not limiting, those skilled in the art know that various modifications may be made to the present invention without departing from the spirit of the present invention, and such modifications also fall within the scope of the invention. On the other hand, examples are provided in the present invention for showing the features and advantages of the antibody of the present invention, but the present invention is not limited to these features and advantages.

The following experimental methods are all conventional methods unless specified otherwise, and the experimental materials used can all be easily obtained from commercial companies unless specified otherwise. The various antibodies used in the following examples of the present invention are all derived from standard antibodies of commercial sources.

Example 1 Antibody Screening

In order to avoid the deviation of the individual immune backgrounds and to ensure the diversity of the antibody library as far as possible, lymphocyte separation solution was used to separate the lymphocytes from the peripheral blood of 162 healthy adults (half male and half female) and the cord blood of 10 newborns (half male and half female) (informed consents were signed for all), and a total of 2×10$^9$ cells were collected. The total RNA was extracted by Trizol method and reversely transcribed into cDNA, and the conventional PCR method was used to amplify the variable region genes of different antibody subtypes. Based on the information of the antibody library vector pDF (Bulletin of the Academy of Military Medical Sciences, 2008, 32(4): 305-308, 358), the restriction sites BssH II, Nhe I, and the linker with Loxp511 sequence (sequence thereof is: SGGSTITSYNVYYTKLSSSGT (SEQ. ID NO: 15)) were introduced, spliced into ScFv (single-chain antibody: VL-Linker (comprising Loxp511 sequence)-VH, with BssH II and Nhe I sites introduced upstream and downstream, respectively) form by overlapping PCR method (for specific method please refer to "Biological Library Technology", edited by Shao Ningsheng et al, Military Medical Science Press, 1st edition, 2011). After separated by electrophoresis, the obtained scFv was enzymatically digested with BssH II and Nhe I, then cloned into the pDF vector enzymatically-digested too, and transformed into E. coli XL1-Blue (Agilent Technology) by electroporation. After amplification culturing with SB medium, 1×10$^{13}$ pfu helper virus VCSM13 (BioVector NTCC Inc.) was added for infection, obtaining a primary phage antibody library with a titer determined as 8×10$^{12}$ cfu/mL. The primary antibody library and BS1365 strain (genotype: F'kan recA1 endA1 gryA96 thi21 ΔlacU169supE44 hsdR17 (λimm434X12cre)) (BioVector NTCC Inc.) were mixed proportionally (Multiplicity of Infection MOI>200), and the loxp/loxp511 recombination was mediated by means of the Cre recombinase expressed by the BS165 strain (for specific method please refer to Hum Antibodies. 1999; 9(1): 67-77; J Biomol Screen. 2014 Feb. 4; 19(6): 839-846), to obtain a large-capacity recombinant antibody library.

Human PD-1 protein expressed by a mammalian cell—Chinese hamster ovary cell CHO-K1 (ATCC® CCL-61™) (a fusion protein of human PD-1 protein extracellular segment-human IgG1 Fc fragment, named hPD1-Fc, wherein the sequence information of human PD-1 refers to NP.054862.1, and the sequence of human IgG1 Fc fragment refers to AEO21920.1) was used as a target to screen the target antibodies. After the hPD1-Fc-coated immuno tubes (Maxisorp ImmunoTube, Thermo Nunc) were blocked with 5% skimmed milk powder, the above-described phage antibody library was added, incubated at 37° C. for 2 hours; removed of the unbound phage and washed 5 times with TBS-T, to sufficiently wash off the non-specifically adsorbed phage; added with 1 mL of elution buffer (0.1 mol/L glycine-HCl, pH 2.2) to elute the phage and neutralized with 40 μL of 2 mol/L Tris solution; added with log phase XL1-Blue bacteria, SB medium (SB medium: 30 g of tryptone, 20 g of yeast extract, 10 g of MOPS, dissolved in 950 mL of deionized water, adjusted with sodium hydroxide to a pH of 7.0, diluted to a volume of 1 L, and autoclaved), and helper phage VCSM13 for amplification and enrichment; the process was repeated for 3-4 rounds, and fresh prepared log phase XL1-Blue bacteria were infected with the eluted phage, coated onto a plate, after incubation at 37° C. overnight, monoclones were randomly picked to seed a 96-well deep well plate (Corning), after amplification culturing, phage-ELISA (for specific method please refer to Bulletin of the Academy of Military Medical Sciences, 2008, 32(4): 305-308, 358) was carried out to determine the binding characteristics thereof to antigens; a total of 165 clones were identified, in which among 48 clones specifically binding to hPD1-Fc, SG001 has the highest binding activity.

The SG001 clone was sequenced, and the obtained variable region gene was analyzed online by IMGT (http://imgt.cines.fr/imgtvquest/vquest). In the obtained SG001 clone, the heavy chain variable region sequence is set forth in SEQ ID NO: 7, of which the amino acid sequences of the three CDRs are SEQ ID NO: 1, SEQ ID NO: 2, and SEQ ID NO: 3, respectively; the sequence of the light chain variable region is SEQ ID NO: 8, and of which the amino acid sequences of the three CDRs are SEQ ID NO: 4, SEQ ID NO: 5, and SEQ ID NO: 6, respectively. The nucleic acid sequence encoding the heavy chain variable region is set forth in SEQ ID NO. 9; and the nucleic acid sequence encoding the light chain variable region is set forth in SEQ ID NO. 10.

Example 2 Expression and Purification of the Antibody

The variable region gene of the obtained SG001 clone was cloned into the eukaryotic expression vector pCMV-163 comprising the human IgG constant region gene, to construct a whole antibody expression vector, the physical map thereof is shown in FIG. 1 (various components of the eukaryotic expression vector pCMV-163 are components known in the art and are recombined in the order as shown). The whole antibody is called SG001 antibody (the light chain amino acid sequence is SEQ ID NO. 11, and the corresponding nucleotide sequence is SEQ ID NO. 12; the heavy chain amino acid sequence is SEQ ID NO. 13, and the corresponding nucleotide sequence is SEQ ID NO. 14). The obtained eukaryotic expression vector was transfected into CHO cells by Lipofectamine 2000 liposome-mediated method and subjected to ELISA assay (the content of the antibodies in the supernatant was determined by double sandwich ELISA using goat anti-human IgG and horseradish peroxidase-labeled goat anti-human IgG, the untransfected supernatant was used as a negative control and the human IgG as a standard) to determine the expression level of the antibodies in the culture supernatant, and a monoclonal cell line with a high expression level was obtained by screening.

For comparison of the properties of the antibody SG001 of the present invention, in the present invention, the light and heavy chain variable region sequences of a similar marketed antibody Nivolumab (Opdivo, Bristol-Myers Squibb) were constructed into the same vector pCMV-163 (the whole antibody is named as BMS01), transfected into CHO cells too, and the expression supernatant was obtained, the supernatant was determined by ELISA for the antibody concentration, and a monoclonal cell line with a higher expression level was obtained by screening. According to the principle of an antibody to play its role, the BMS01 antibody has the same activity as that of the marketed antibody Nivolumab, and can be used as a positive control for the antibody of the present invention.

Figure 2:
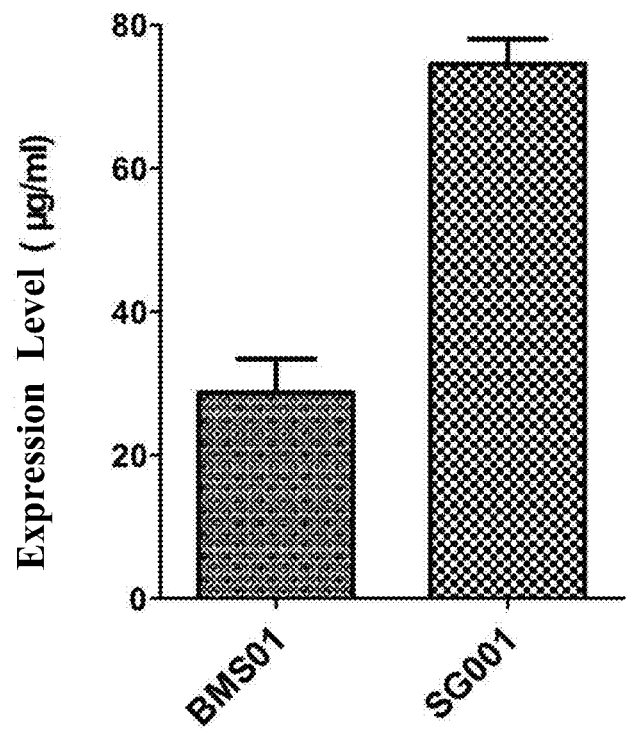
FIG. 2 shows the antibody expression level in the cell culture supernatant determined by double sandwich ELISA.

The ELISA assay results showed that the antibodies were expressed in both expression supernatants of the SG001 antibody and the BMS01 antibody. With the same expression vectors, cells and under the same expression conditions, the expression level of the SG001 antibody was about 2-3 times of the expression level of the BMS01 antibody (SG001 74.5±4.9 ug/mL vs BMS01 28.7±6.6, P=0.016). The results were shown in FIG. 2.

Sufficient supernatant was collected and the target antibodies were purified using conventional Protein A affinity purification.

Example 3 Analysis on Specific Binding Activity of the Antibody

Figure 3:
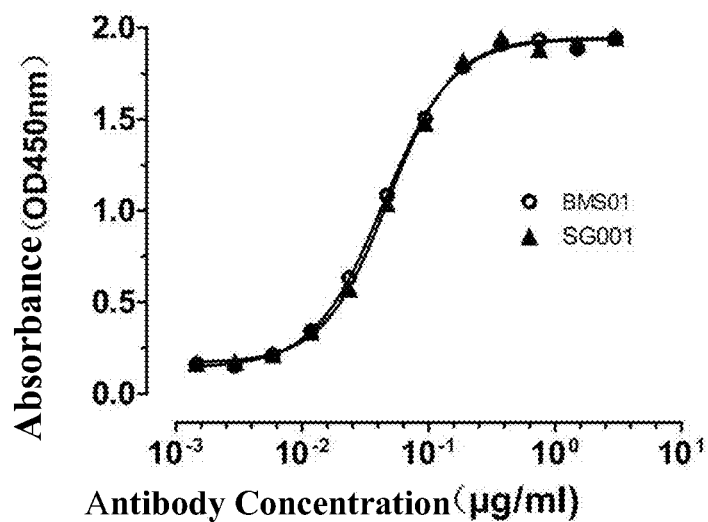
FIG. 3 shows that both of SG001 antibody and BMS01 positive antibody specifically recognize target antigen human PD1.

An ELISA plate was coated with the target antigen hPD1-Fc, 1 ug/ml, 4° C. overnight; washed with PBST and then added with 1.5% casein, and blocked overnight at 4° C.; added with the SG001 antibody or BMS01 antibody of different concentrations, and reacted at 37° C. for 2 hours; washed with PBST, added with horseradish peroxidase-labeled goat anti-human Fab secondary antibodies (GAH-Fab-HRP, Abcam), and reacted for 45 minutes at room temperature; the plate was washed 5 times with PBST and patted on a drying paper to dry out the residual droplets as possible; added with 100 μl of TMB/well, and placed in the dark for 3 min at room temperature (20±5° C.); 100 μl of 2N $H_2SO_4$ stop solution/well was added to stop the substrate reaction, and the microplate reader was read at 450 nm for the $OD_{450}$ value, the binding ability of the antibody to the target antigen hPD1-Fc was analyzed. Both the SG001 antibody and the BMS01 positive antibody can specifically recognize the target antigen hPD1-Fc; the recognition activity exhibited significant dose dependency, and the results were shown in FIG. 3.

ELISA plates were coated with various CD28 family members hPD1-FC, CD28, CTLA4, BTLA and ICOS (Beijing Sino Biological Inc.), respectively, 1 ug/ml, 4° C. overnight; washed with PBST and then added with 1.5% casein, and blocked overnight at 4° C.; added with the SG001 antibody or the BMS01 antibody of different concentrations, and reacted at 37° C. for 2 hours; washed with PBST, then added with horseradish peroxidase-labeled goat anti-human Fab secondary antibodies (GAH-Fab-HRP), and reacted for 45 minutes at room temperature; the plate was washed 5 times with PBST and patted on a drying paper to dry out the residual droplets as possible; added with 100 μl of TMB/well, and placed in the dark for 3 min at room temperature (20±5° C.); 100 μl of 2N $H_2SO_4$ stop solution was added to each well to stop the substrate reaction, and the microplate reader was read at 450 nm for the OD value, the binding ability of the antibodies to each CD28 family member were analyzed.

Figure 4:
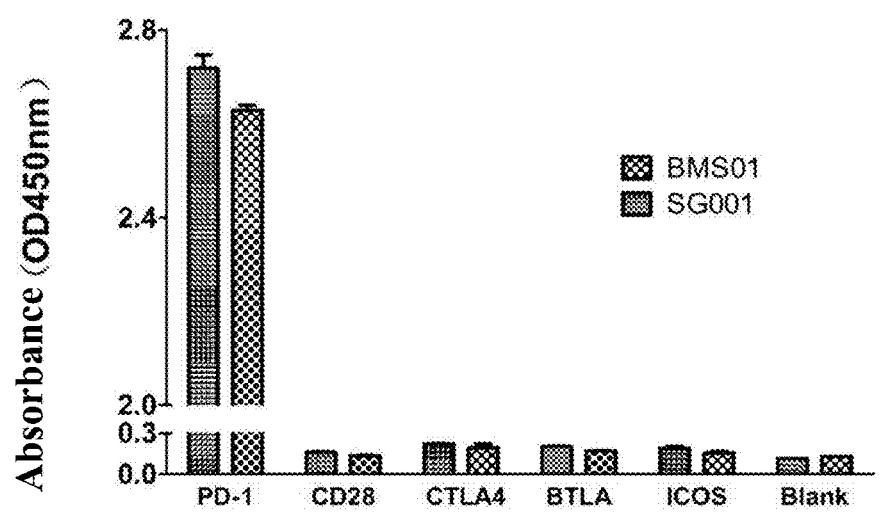
FIG. 4 shows that neither SG001 antibody nor BMS01 positive antibody specifically binds to other members of CD28 family.

The results showed that both the SG001 antibody and the BMS01 positive antibody can specifically recognize the target antigen hPD1-Fc, and exhibited significant dose dependency; no significant binding reaction was observed between the SG001 antibody or the BMS01 positive antibody and the CD28, CTLA4, BTLA and ICOS or other CD28 family members; and the results were shown in FIG. 4.

Example 4 Analysis on the Antibody Affinity

The antibody affinity was analyzed using BIACORE Biomacromolecular Interaction Device (GE). The anti-human IgG-Fab antibody (Abcam) was conjugated on a chip, the anti-human IgG-Fab antibody was used to capture the SG001 antibody or the BMS01 positive antibody, the antibody concentration was set to 1 μg/mL, and the sample injection time was 60-150 seconds; the antigen hPD1-FC was used as a mobile phase, and 6 concentration gradients (3.125, 6.25, 12.5, 25, 50, 100 nM) were used, with a binding time of 120 seconds; the dissociation time was 1200S; 10 mM glycine-hydrochloric acid buffer (pH 2.1) was used for regeneration, for a period of 60S. The results showed that the affinities of the SG001 antibody and the BMS01 positive antibody were 2.15 nM and 1.4 nM, respectively, which were substantially same. The results were shown in Table 1.

TABLE 1

Determination results for the affinities of the SG001 antibody and the BMS01 positive antibody

| Antibody | Association constant Ka (1/Ms) | Dissociation constant Kd (1/s) | Affinity constant KD (M) |
| --- | --- | --- | --- |
| BMS01 | $5.594 \times 10^5$ | $7.900 \times 10^{-5}$ | $1.412 \times 10^{-10}$ |
| SG001 | $3.184 \times 10^5$ | $6.850 \times 10^{-5}$ | $2.151 \times 10^{-10}$ |

Example 5 Competition of SG001 Antibody with BMS01 Positive Antibody in Recognizing Antigens hPD1-FC proteins were diluted in a coating buffer at a coating concentration of 1 μg/mL, and then added to the wells of a coated plate in an amount of 100 μl/well, and the plate was coated at 4° C. overnight; the plate was washed 3 times with a washing solution (PBS+0.2% Tween 20) repeatedly, added with 1.5% casein at 200 μl/well to the corresponding wells, and blocked at 37° C. for 1 h. The Biotin-labeled BMS01 antibody (BMS01-Biotin) was diluted with PBS buffer to 0.5 μg/mL, and the antibodies SG001 and BMS01 to be determined were diluted with this antibody solution, respectively. The highest concentration for SG001 and BMS01 was 400 μg/mL, and multiple proportion dilution was performed to set 12 concentrations; the gradiently-diluted antibody solutions were added to the blocked ELISA reaction wells, with 100 μl per well, and for each sample concentration 2 parallel duplicate wells were set, the plate was covered by a plate sealer, and placed at 37° C. for 1.5 hours. The plate was washed 3 times with a washing solution repeatedly, added with HRP-labeled avidin, and placed in the dark at room temperature (20±5° C.) for 45 minutes. The plate was washed 5 times with a washing solution repeatedly, and patted on a drying paper to dry out the residual droplets as possible; added with 100 μl of TMB to each well, and placed in the dark for 3 min at room temperature (20±5° C.); 100 μl of 2N $H_2SO_4$ stop solution was added to each well to stop the substrate reaction, and the microplate reader was read at 450 nm for the OD value.

Figure 5:
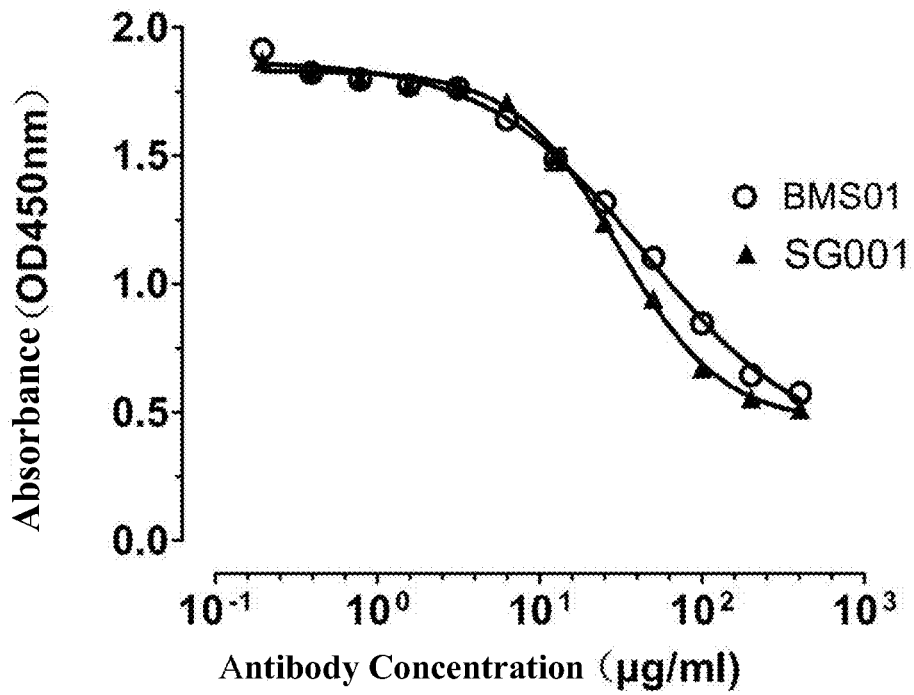
FIG. 5 shows that SG001 antibody specifically competes with BMS01 positive antibody for recognition of the target antigen.

The results showed that both the SG001 antibody and the BMS01 positive antibody were able to competitively inhibit the binding of BMS01-Biotin to the antigen hPD1-FC, and exhibited a dose dependency; there was no significant difference between the SG001 antibody and the BMS01 positive antibody; and the results were shown in FIG. 5.

Example 6 The Antibody Blocking the Interaction Between PD1 and PDL1 hPDL1 proteins (product of Sino Biological Inc.) were diluted in a coating buffer at a concentration of 1 μg/mL, and added to each well of an ELISA plate in an amount of 100 μl/well, and the plate was coated at 4° C. overnight. The plate was washed 3 times with a washing solution repeatedly, added in each well with 200 μl of 1.5% casein, and blocked at 37° C. for 1 h. The hPD1-FC-Biotin (Biotin labeled hPD1-FC proteins, wherein the hPD1-FC was obtained from Example 1 and entrusted with Jiaxuan Biotech to do the labeling) was diluted with PBS buffer to 5 μg/mL, and the antibodies SG001, BMS01 to be determined were diluted with this solution. The highest concentration of SG001 and BMS01 was 500 μg/mL, and according to the preliminary experiment, SG001 was diluted 5 folds, and BMS01 was diluted 4 folds, with 8 concentrations each; the gradiently-diluted antibody solutions were added to the blocked ELISA reaction wells, with 100 μl per well, and for each sample concentration 2 parallel duplicate wells were set, the plate was covered by a plate sealer, and placed at 37° C. for 1.5 hours horizontally. The plate was washed 3 times with a washing solution repeatedly, added with HRP-labeled avidin, and placed in the dark at room temperature (20±5° C.) for 45 minutes. The plate was washed 5 times with a washing solution repeatedly, and patted on a drying paper to dry out the residual droplets as possible; added with 100 μl of TMB to each well, and placed in the dark for 3 min at room temperature (20±5° C.); 100 μl of 2N $H_2SO_4$ stop solution was added to each well to stop the substrate reaction, and the microplate reader was read at 450 nm for the OD value. The antibodies were analyzed for their ability to block the interaction between PD1 and PDL1.

Figure 6:
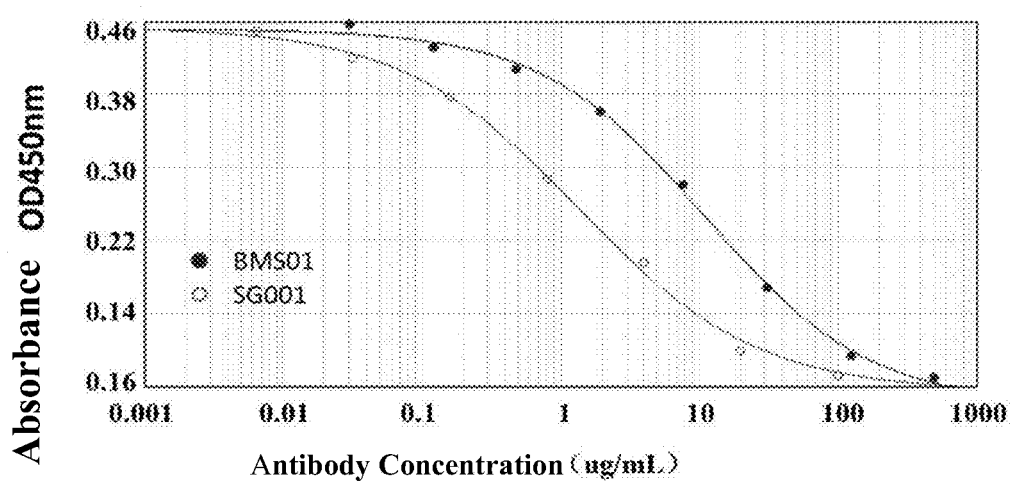
FIG. 6 shows that both of SG001 antibody and BMS01 positive antibody specifically block PD1/PDL1 interaction.

The results showed that both the SG001 antibody and the BMS01 positive antibody were able to block the binding of hPDL1 to hPD1-FC, and exhibited a dose dependency; the half inhibitory dosage for the SG001 antibody was 1.47±0.227 μg/mL, which was significantly superior to that for the positive antibody BMS01 (10.62±0.536 μg/mL), $P<0.0001$). The results were shown in FIG. 6.

Example 7 The Antibody Blocking the Interaction Between PD1 and PDL2

PDL2 proteins (Beijing Sino Biological Inc.) were diluted in a coating buffer at a concentration of 1 μg/mL, and added to each well of an ELISA plate in an amount of 100 μl/well, and the plate was coated at 4° C. overnight. The plate was washed 3 times with a washing solution repeatedly, added in each well with 200 μl of 1.5% casein, and blocked at 37° C. for 1 h. The hPD1-FC-Biotin (Biotin labeled hPD1-FC proteins, wherein the hPD1-FC was obtained from Example 1 and entrusted with Jiaxuan Biotech to do the labeling) was diluted with PBS buffer to 10 μg/mL, and the antibodies SG001, BMS01 to be determined were diluted with this solution. The highest concentration of SG001 and BMS01 was 100 μg/mL, and multiple proportion dilution was performed to set 12 concentrations totally; the gradiently-diluted antibody solutions were added to the blocked ELISA reaction wells, with 100 μl per well, and for each sample concentration 2 parallel duplicate wells were set, the plate was covered by a plate sealer, and placed at 37° C. for 1.5 hours horizontally. The plate was washed 3 times with a washing solution repeatedly, added with HRP-labeled avidin, and placed in the dark at room temperature (20±5° C.) for 45 minutes. The plate was washed 5 times with a washing solution repeatedly, and patted on a drying paper to dry out the residual droplets as possible; added with 100 μl of TMB to each well, and placed in the dark for 3 min at room temperature (20±5° C.); 100 μl of 2N $H_2SO_4$ stop solution was added to each well to stop the substrate reaction, and the microplate reader was read at 450 nm for the OD value. The antibodies were analyzed for their ability to block the interaction between PD1 and PDL2.

Figure 7:
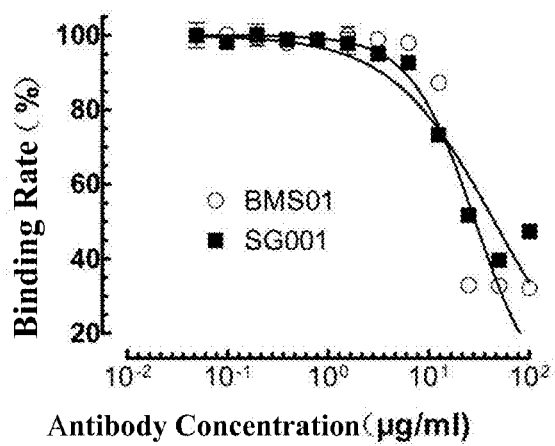
FIG. 7 shows that both of SG001 antibody and BMS01 positive antibody specifically block PD1/PDL2 interaction.

The results showed that both the SG001 antibody and the BMS01 positive antibody were able to block the interaction between hPD1-FC-Biotin and PDL2, and exhibited a dose dependency; there was no significant difference between the SG001 antibody and the BMS01 positive antibody. The results were shown in FIG. 7.

Example 8 The Antibody Recognizing Monkey PD1 Antigen

ELISA plates were coated with the monkey PD1 (Sino Biological Inc.) and the hPD1-Fc, respectively, at 1 ug/ml, 4° C. overnight; washed with PBST, added with 1.5% casein, and blocked overnight at 4° C.; added with the SG001 antibody or the BMS01 antibody of different concentrations, and reacted at 37° C. for 2 hours; washed with PBST, added with horseradish peroxidase-labeled goat anti-human Fab secondary antibodies (GAH-Fab-HRP), and reacted for 45 minutes at room temperature; the plate was washed 5 times with PBST and patted on a drying paper to dry out the residual droplets as possible; added with 100 μl of TMB to each well, and placed in the dark for 3 min at room temperature (20±5° C.); 100 μl of 2N $H_2SO_4$ stop solution was added to each well to stop the substrate reaction, and the microplate reader was read at 450 nm for the OD value, to analyze the binding ability of the antibodies to the monkey PD1.

Figure 8A:
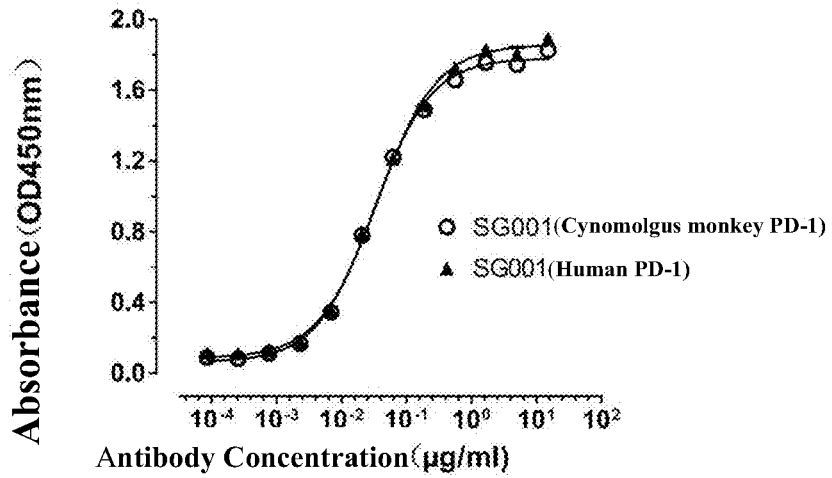
FIG. 8A shows that SG001 antibody specifically recognizes monkey PD1 and human PD1.
Figure 8B:
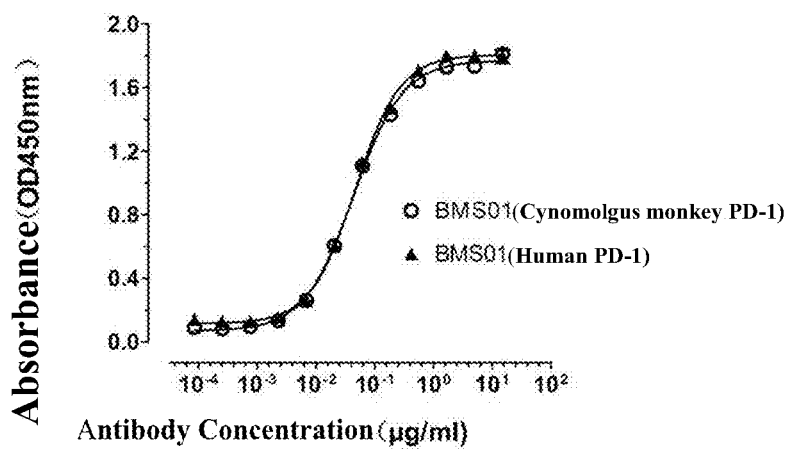
FIG. 8B shows that BMS01 positive antibody specifically recognizes monkey PD1 and human PD1.

Both the SG001 antibody (FIG. 8A) and the BMS01 positive antibody (FIG. 8B) were able to specifically recognize the monkey PD1 protein, and exhibited a significant dose dependency; there was no significant difference between the activity of the antibodies in recognizing the monkey PD1 protein.

Example 9 The Antibody Enhancing the Immune Response In Vitro

The peripheral blood from a healthy person was taken, and the peripheral blood mononuclear cells (PBMCs) were isolated using the lymphocyte separation solution (Tianjin Haoyang Biological Manufacture Co., Ltd.), and the mononuclear cells were further isolated from the PBMCs using a mononuclear cell isolation kit (Miltenyi); the cell concentration was adjusted, and the cells were inoculated on a 96-well cell culture plate at $2×10^4$/well, the culture system being a 1640 medium, containing 10% of fetal bovine serum, 25 ng/ml GM-SCF (BioLegend) and 50 ng/ml IL-4 (BioLegend); 37° C., 5% $CO_2$, conventional culture; replaced with fresh medium every 3 days, cultured for 7 days, and the dendritic cells (DCs) were induced.

On day 7 of the experiment, another healthy human blood was taken and the PBMCs were isolated; a CD4 positive T cell ($CD4^+T$) sorting kit (eBioscience) was used to further isolate the $CD4^+T$ cells from the isolated PBMCs; the cell concentration was adjusted, and the cells were inoculated on the aforementioned DC cell-inducing culture plate at $2×10^5$/ well. The SG001 antibody and the BMS01 positive antibody were added, respectively, with a gradient-concentration of 0.016, 0.08, 0.4, 2, 10, 50 μg/ml, with 3 duplicate wells set; a negative group (only CD4+T, DCs and CD4+T combined DCs) was set in the experiment.

The supernatant was harvested after 5 days of conventional culture at 37° C., 5% $CO_2$, and the expression level of IFN-γ in the supernatant was determined.

Figure 9:
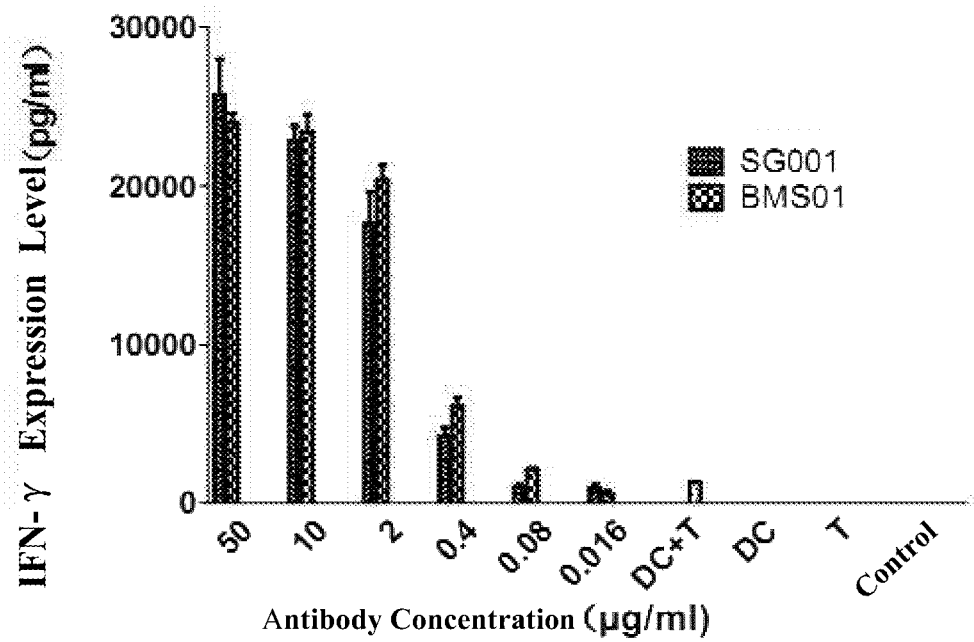
FIG. 9 shows that both of SG001 antibody and BMS01 positive antibody enhance immune response in vitro.

The results showed (FIG. 9) that IFN-γ was expressed at a background level in the culture supernatant of the one having only CD4+T cells, DCs and CD4+T combined DCs; the expression of IFN-γ was significantly increased after addition of antibodies of different gradient-concentrations, with a dose dependency; and there was no significant difference between the SG001 antibody and the BMS01 positive antibody.

Example 10 The Antibody Enhancing the Immune Response In Vivo

The peripheral blood of a healthy person was taken, and the peripheral blood mononuclear cells (PBMCs) were isolated using the lymphocyte separation solution (Tianjin Haoyang Biological Manufacture Co., Ltd.); the 1640 medium (free of serum) was used to adjust the concentration of the PBMCs to $5×10^6$/ml, and the resultant was injected into the tail vein of NPG mice (immuno-deficient type mice, product of Vitalstar), 200 μl per mouse, to establish a graft-versus-host disease (GVHD) model of the human PMBC-transplanted mice; the experiment was divided into three groups, each group was administered with the SG001 antibody, the BMS01 positive antibody and physiological saline, at an antibody dose of 150 μg/mouse, twice a week for 2 weeks; and the biological function of the anti-PD1 antibody in enhancing the immune response in vivo was analyzed; the mice was weighed every five days, the survival time of the mice was recorded and the survival rate was calculated.

Figure 10:
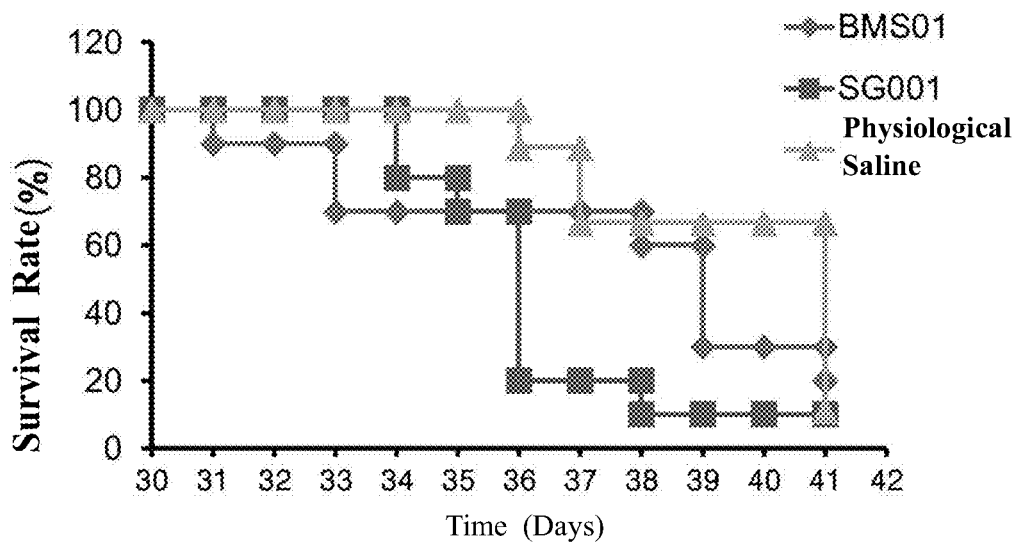
FIG. 10 shows that both of SG001 antibody and BMS01 positive antibody enhance immune response in vivo.

The weight of the PMBC-transplanted mice was gradually increased at an early stage, and began to decrease after 20 days, the mice developed a GVHD response, and then began to die (FIG. 10), the median survival time of the saline control group was 41 days, the median survival times of the SG001 antibody and the BMS01 positive antibody groups were 36 days and 39 days, respectively, the survival rate of the mice was decreased (SG001 vs NC, P=0.0044; BMS01 vs NC, P=0.5240), the survival time was shortened, indicating that the GVHD effect was intensified; as compared to the BMS01 positive antibody group, the average survival time of the mice in the SG001 antibody group was shorter, indicating that the GVHD effect was more significant (SG001 vs BMS01, P=0.0827). The experimental results indicated that both the SG001 antibody and the BMS01 positive antibody can enhance the immune response in vivo, and the SG001 antibody had slightly better activity than the BMS01 positive antibody.

Example 11 The Antibody Inhibiting the Tumor Growth

The antibody heavy-chain constant region gene in the eukaryotic expression vector obtained in Example 2 was replaced with the constant region gene of the human IgG4 subtype, and the SG001 antibody of the IgG4 subtype (SG001-IgG4, the light chain amino acid sequence is SEQ ID NO. 11, and the heavy chain amino acid sequence is SEQ ID NO. 16) was constructed, and the sample SG001-IgG4 was prepared with reference to the methods and procedures of Example 2.

The activity of the PD1 antibody in inhibiting the tumor growth was evaluated by establishing a tumor model by inoculating murine intestinal cancer MC38 cells (product of American ATCC) into PD-1 humanized B-hPD-1 mice. Male, 4- to 6-week-old B-hPD-1 mice (product of Beijing Biocytogen Co., Ltd) were selected. After thawing of the murine intestinal cancer MC38 cells to a desired amount, the log phase growth cells were collected and suspended to a concentration of $10^7$ cells/mL, and 0.1 mL ($1×10^6$ cells) was subcutaneously inoculated to the B-hPD-1 mice. The animals were observed daily and checked with the tumor growth, when the average tumor size was 100 $mm^3$, they were randomly grouped and started to be administered, a physiological saline control group, a SG001-IgG4 group and a Nivolumab group (Japan Squibb Co., Ltd.) were set; the administration was started on day 6 after the transplantation, at an administration dose of 20 mg/kg, with an administration cycle of once every 4 days, 6 times in total, and the body weight and tumor growth of the mice were observed.

Figure 11:
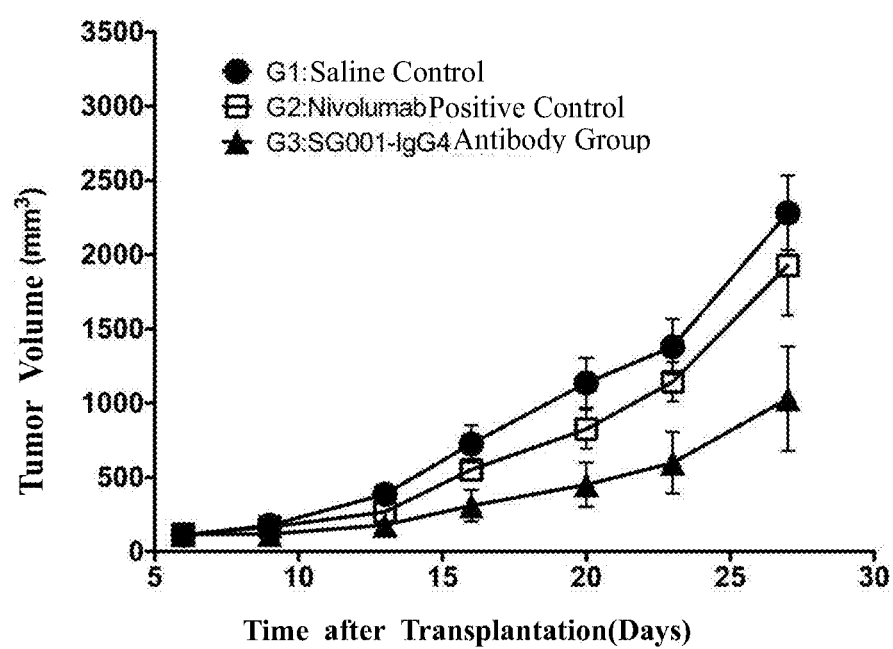
FIG. 11 shows that both of SG001-IgG4 antibody and Nivolumab positive antibody inhibit tumor growth.

The results showed that the anti-PD-1 antibody positive reference drug (the original drug Nivolumab) and the SG001-IgG4 antibody used in the experiment were both accepted by the experimental animals, the body weights of the animals showed a continuous increase, and there was no significant difference between the administration group and the negative antibody control group. As compared to the solvent control group, each administration group of the animals showed significant tumor growth inhibition (FIG. 11). The average tumor inhibition rate was 16% in the Nivolumab group, and the average tumor inhibition rate was 58% in the SG001-IgG4 group, there was a statistically difference between the SG001-IgG4 group and the Nivolumab group (P<0.05).

What is claimed is:

1. An isolated anti-human programmed death 1 receptor (anti-hPD-1) antibody or an antigen-binding fragment thereof, wherein a CDR1 sequence of a heavy chain variable region thereof is set forth in SEQ ID NO: 1, a CDR2 sequence is set forth in SEQ ID NO: 2, and a CDR3 sequence is set forth in SEQ ID NO: 3; and a CDR1 sequence of a light chain variable region thereof is set forth in SEQ ID NO: 4, a CDR2 sequence is set forth in SEQ ID NO: 5, and a CDR3 sequence is set forth in SEQ ID NO: 6.

2. The anti-hPD-1 antibody or the antigen-binding fragment thereof according to claim 1, wherein a heavy chain variable region sequence thereof is set forth in SEQ ID NO: 7; and a light chain variable region sequence thereof is set forth in SEQ ID NO: 8.

3. The anti-hPD-1 antibody or the antigen-binding fragment thereof according to claim 1, wherein a heavy chain amino acid sequence thereof is set forth in SEQ ID NO: 13 or 16; and a light chain amino acid sequence thereof is set forth in SEQ ID NO: 11.

4. The anti-hPD-1 antibody or the antigen-binding fragment thereof according to claim 1, wherein the antibody is a full-length antibody, and preferably, a full-length antibody of an IgG1 or IgG4 isotype.

5. The anti-hPD-1 antibody or the antigen-binding fragment thereof according to claim 2, wherein the antibody is a full-length antibody, and preferably, a full-length antibody of an IgG1 or IgG4 isotype.

6. The anti-hPD-1 antibody or the antigen-binding fragment thereof according to claim 3, wherein the antibody is a full-length antibody, and preferably, a full-length antibody of an IgG1 or IgG4 isotype.

7. The anti-hPD-1 antibody or the antigen-binding fragment thereof according to claim 1, which is an antigen-binding fragment, and preferably, a Fab fragment, a Fab'2 fragment or a single-chain antibody.

8. A nucleic acid molecule encoding the anti-hPD-1 antibody or the antigen-binding fragment thereof according to claim 1.

9. The nucleic acid molecule according to claim 8, which has a sequence set forth in SEQ ID NO: 9 or 10.

10. The nucleic acid molecule according to claim 8, which has a sequence set forth in SEQ ID NO: 12 or 14.

11. A method of regulating immune response by specifically blocking PD1/PDL1 signaling pathway in a mammal comprising administering to the mammal the antibody or the antigen-binding fragment thereof according to claim 1.

12. The method according to claim 11, wherein regulating immune response by specifically blocking the PD1/PDL1 signaling pathway inhibits growth of a tumor.

13. The method according to claim 12, wherein the tumor is an intestinal cancer.

14. The method according to claim 11, wherein the mammal is a human.

* * * * *

SEQUENCE LISTING

```
<160> NUMBER OF SEQ ID NOS: 16

<210> SEQ ID NO 1
<211> LENGTH: 8
<212> TYPE: PRT
<213> ORGANISM: Artificial sequence
<220> FEATURE:
<223> OTHER INFORMATION: Heavy chain CDR1

<400> SEQUENCE: 1

Gly Leu Thr Phe Ser Ser Ser Gly
1               5
```

```
<210> SEQ ID NO 2
<211> LENGTH: 8
<212> TYPE: PRT
<213> ORGANISM: Artificial sequence
<220> FEATURE:
<223> OTHER INFORMATION: Heavy chain CDR2

<400> SEQUENCE: 2

Ile Trp Tyr Asp Gly Ser Lys Arg
1               5

<210> SEQ ID NO 3
<211> LENGTH: 6
<212> TYPE: PRT
<213> ORGANISM: Artificial sequence
<220> FEATURE:
<223> OTHER INFORMATION: Heavy chain CDR3

<400> SEQUENCE: 3

Ala Thr Asn Asn Asp Tyr
1               5

<210> SEQ ID NO 4
<211> LENGTH: 11
<212> TYPE: PRT
<213> ORGANISM: Artificial sequence
<220> FEATURE:
<223> OTHER INFORMATION: Light chain CDR1

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Artificial sequence
<220> FEATURE:
<223> OTHER INFORMATION: Light chain CDR2

<400> SEQUENCE: 5

Thr Ala Ser Asn Arg Ala Thr
1               5

<210> SEQ ID NO 6
<211> LENGTH: 9
<212> TYPE: PRT
<213> ORGANISM: Artificial sequence
<220> FEATURE:
<223> OTHER INFORMATION: Light chain CDR3

<400> SEQUENCE: 6

Gln Gln Tyr Ser Asn Trp Pro Arg Thr
1               5

<210> SEQ ID NO 7
<211> LENGTH: 113
<212> TYPE: PRT
<213> ORGANISM: Artificial sequence
<220> FEATURE:
<223> OTHER INFORMATION: Heavy chain variable region

<400> SEQUENCE: 7

Gln Val Gln Leu Val Glu Ser Gly Gly Gly Val Val Gln Pro Gly Arg
1               5                   10                  15
```

Ser Leu Arg Leu Thr Cys Lys Ala Ser Gly Leu Thr Phe Ser Ser
            20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
 50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser

<210> SEQ ID NO 8
<211> LENGTH: 107
<212> TYPE: PRT
<213> ORGANISM: Artificial sequence
<220> FEATURE:
<223> OTHER INFORMATION: Light chain variable region

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Thr Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Asn Trp Pro Arg
                85                  90                  95

Thr Phe Gly Gln Gly Thr Lys Val Glu Ile Lys
            100                 105

<210> SEQ ID NO 9
<211> LENGTH: 339
<212> TYPE: DNA
<213> ORGANISM: Artificial sequence
<220> FEATURE:
<223> OTHER INFORMATION: Nucleotide sequence encoding heavy chain
      variable region

<400> SEQUENCE: 9
caggtgcagc tggtggagag cggcggcggc gtggtgcagc tggcagaaag cctgagactg     60
acctgcaagg ccagcggcct caccttcagc agcagcggca tgcactgggt gagacaggcc    120
cctggcaagg gcctggagtg ggtggccgtg atctggtacg acggcagcaa gcggtactac    180
gccgacagcg tgaagggcag attcaccatc agcagagaca acagcaagaa caccctgttc    240
ctgcagatga acagcctgag agccgaggac accgccgtgt actactgcgc caccaacaac    300
gactactggg gccagggcac cctggtgacc gtgagcagc                           339

<210> SEQ ID NO 10
<211> LENGTH: 321
<212> TYPE: DNA
<213> ORGANISM: Artificial sequence
<220> FEATURE:
<223> OTHER INFORMATION: Nucleotide sequence encoding light chain
     variable region

<400> SEQUENCE: 10

```
gagatcgtgc tgacccagag ccctgccacc ctgagcctga gccctggcga gagagccacc    60
ctgagctgca gagccagcca gagcgtgagc agctacctgg cctggtacca gcagaagcct   120
ggccaggccc ctagactgct gatctacacc gccagcaaca gagccaccgg catccctgcc   180
agattcagcg gcagcggcag cggcaccgac ttcaccctga ccatcagcag cctggagcct   240
gaggacttcg ccgtgtacta ctgccagcag tacagcaact ggcctagaac cttcggccag   300
ggcaccaagg tggagatcaa g                                             321
```

<210> SEQ ID NO 11
<211> LENGTH: 214
<212> TYPE: PRT
<213> ORGANISM: Artificial sequence
<220> FEATURE:
<223> OTHER INFORMATION: Light chain amino acid sequence

<400> SEQUENCE: 11

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Thr Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 645
<212> TYPE: DNA
<213> ORGANISM: Artificial sequence
<220> FEATURE:
<223> OTHER INFORMATION: Nucleotide sequence encoding light chain amino
     acid sequence

<400> SEQUENCE: 12

```
gagatcgtgc tgacccagag ccctgccacc ctgagcctga gccctggcga gagagccacc      60
ctgagctgca gagccagcca gagcgtgagc agctacctgg cctggtacca gcagaagcct     120
ggccaggccc ctagactgct gatctacacc gccagcaaca gagccaccgg catccctgcc     180
agattcagcg gcagcggcag cggcaccgac ttcaccctga ccatcagcag cctggagcct     240
gaggacttcg ccgtgtacta ctgccagcag tacagcaact ggcctagaac cttcggccag     300
ggcaccaagg tggagatcaa agcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg ataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                      645
```

<210> SEQ ID NO 13
<211> LENGTH: 443
<212> TYPE: PRT
<213> ORGANISM: Artificial sequence
<220> FEATURE:
<223> OTHER INFORMATION: Heavy chain amino acid sequence

<400> SEQUENCE: 13

```
Gln Val Gln Leu Val Glu Ser Gly Gly Gly Val Val Gln Pro Gly Arg
1               5                   10                  15

Ser Leu Arg Leu Thr Cys Lys Ala Ser Gly Leu Thr Phe Ser Ser Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240
```

```
Pro Lys Pro Lys Asp Thr Leu Met Ile Ser Arg Thr Pro Glu Val Thr
            245                 250                 255

Cys Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 14
<211> LENGTH: 1332
<212> TYPE: DNA
<213> ORGANISM: Artificial sequence
<220> FEATURE:
<223> OTHER INFORMATION: Nucleotide sequence encoding heavy chain amino
      acid sequence

<400> SEQUENCE: 14
caggtgcagc tggtggagag cggcggcggc gtggtgcagc tggcagaaag cctgagactg      60
acctgcaagg ccagcggcct caccttcagc agcagcggca tgcactgggt gagacaggcc     120
cctggcaagg gcctggagtg ggtggccgtg atctggtacg acggcagcaa gcggtactac     180
gccgacagcg tgaagggcag attcaccatc agcagagaca cagcaagaa caccctgttc      240 ctgcagatga acagcctgag agccgaggac accgccgtgt actactgcgc caccaacaac     300
gactactggg gccagggcac cctggtgacc gtgagcagcg ctagcaccaa gggcccatcg     360
gtcttccccc tggcaccctc ctccaagagc acctctgggg gcacagcggc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acccagacct acatctgcaa cgtgaatcac     600
aagcccagca acaccaaggt ggacaagaaa gttgagccca aatcttgtga caaaactcac     660
acatgcccac cgtgcccagc acctgaactc ctggggggac cgtcagtctt cctcttcccc     720
ccaaaaccca aggacaccct catgatctcc cggacccctg aggtcacgtg cgtggtggtg     780
gacgtgagcc acgaagaccc cgaggtcaag ttcaactggt acgtggacgg cgtggaggtg     840
cataatgcca agacaaagcc gcgggaggag cagtacaaca gcacgtaccg tgtggtcagc     900
```

```
gtcctcaccg tcctgcacca ggactggctg aatggcaagg agtacaagtg caaggtctcc      960
aacaaagccc tcccagcccc catcgagaaa accatctcca agccaaagg gcagccccga      1020 gaaccacagg tgtacaccct gccccatcc cgggatgagc tgaccaagaa ccaggtcagc      1080
ctgacctgcc tggtcaaagg cttctatccc agcgacatcg ccgtggagtg ggagagcaat      1140
gggcagccgg agaacaacta caagaccacg cctcccgtgc tggactccga cggctccttc      1200
ttcctctaca gcaagctcac cgtggacaag agcaggtggc agcaggggaa cgtcttctca      1260
tgctccgtga tgcatgaggc tctgcacaac cactacacgc agaagagcct ctccctgtct      1320
ccgggtaaat ga                                                          1332
```

<210> SEQ ID NO 15
<211> LENGTH: 21
<212> TYPE: PRT
<213> ORGANISM: Artificial sequence
<220> FEATURE:
<223> OTHER INFORMATION: Loxp511 sequence

<400> SEQUENCE: 15

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 16
<211> LENGTH: 440
<212> TYPE: PRT
<213> ORGANISM: Artificial sequence
<220> FEATURE:
<223> OTHER INFORMATION: Heavy chain amino acid sequence

<400> SEQUENCE: 16

Gln Val Gln Leu Val Glu Ser Gly Gly Gly Val Val Gln Pro Gly Arg
1               5                   10                  15

Ser Leu Arg Leu Thr Cys Lys Ala Ser Gly Leu Thr Phe Ser Ser Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asn Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

-continued

```
Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440
```